(12) United States Patent
Cho

(10) Patent No.: US 11,513,065 B2
(45) Date of Patent: Nov. 29, 2022

(54) ELECTRONIC DEVICE

(71) Applicant: SK hynix Inc., Icheon-si (KR)

(72) Inventor: Min Su Cho, Seongnam-si (KR)

(73) Assignee: SK hynix Inc., Icheon-si (KR)

( * ) Notice: Subject to any disclaimer, the term of this patent is extended or adjusted under 35 U.S.C. 154(b) by 288 days.

(21) Appl. No.: 16/846,687

(22) Filed: Apr. 13, 2020

(65) Prior Publication Data

US 2021/0088439 A1 Mar. 25, 2021

(30) Foreign Application Priority Data

Sep. 25, 2019 (KR) ........................ 10-2019-0118289

(51) Int. Cl.
| | | |
|---|---|---|
| *G01N 21/31* | (2006.01) | |
| *G01N 33/00* | (2006.01) | |
| *G01N 21/25* | (2006.01) | |
| *H01L 27/146* | (2006.01) | |
| *G01J 1/04* | (2006.01) | |

(52) U.S. Cl.
CPC .......... *G01N 21/314* (2013.01); *G01J 1/0488* (2013.01); *G01N 21/255* (2013.01); *G01N 33/0031* (2013.01); *H01L 27/14621* (2013.01); *H01L 27/14623* (2013.01); *H01L 27/14627* (2013.01); *H01L 27/14645* (2013.01); *G01N 2021/3181* (2013.01)

(58) Field of Classification Search
CPC ......... H01L 27/14645; H01L 27/14643; H01L 27/14627; H01L 27/14625; H01L 27/14623; H01L 27/14621; H01L 27/1461; H01L 27/14609; H01L 27/14601; H01L 27/146; G01J 1/0492; G01J 1/0488; G01N 33/0009; G01N 33/0027; G01N 33/0031; G01N 2021/3181; G01N 21/25; G01N 21/255; G01N 21/31; G01N 21/314
See application file for complete search history.

(56) References Cited

U.S. PATENT DOCUMENTS

| | | | | |
|---|---|---|---|---|
| 2021/0088439 A1* | 3/2021 | Cho | ..................... | G01J 1/0488 |
| 2021/0280625 A1* | 9/2021 | Park | ..................... | H01L 27/1464 |

FOREIGN PATENT DOCUMENTS

| | | |
|---|---|---|
| KR | 10-2013-0033967 A | 4/2013 |
| KR | 10-1674802 B1 | 11/2016 |

* cited by examiner

*Primary Examiner* — John R Lee
(74) *Attorney, Agent, or Firm* — Perkins Coie LLP

(57) ABSTRACT

An electronic device includes at least one grid structure that extends in rows and columns of a pixel array including a plurality of imaging pixels and is structured to separate the imaging pixels from one another to provide optical isolation between two adjacent imaging pixels, a grid shutter coupled to the grid structure and configured to allow a gas to enter the grid structure by opening a passage for the gas or block the gas from entering the grid structure by closing the passage in the grid structure, and a gas detection controller configured to identify the gas flowing into the grid structure based on an image that is acquired by the image sensor when the passage for the gas in the grid structure is opened to allow the gas to be present in the grid structure.

20 Claims, 12 Drawing Sheets

|       | C1  | C2  | C3  | ... | C24 |
|-------|-----|-----|-----|-----|-----|
| Gas 1 | 117 | 99  | 99  | ... | 197 |
| Gas 2 | 41  | 9   | 178 | ... | 99  |
| Gas 3 | 61  | 125 | 86  | ... | 163 |
| ⋮     | ⋮   | ⋮   | ⋮   | ⋱   | ⋮   |
| Gas n | 108 | 65  | 151 | ... | 232 |

FIG.10

ELECTRONIC DEVICE

CROSS-REFERENCE TO RELATED APPLICATION

This patent document claims the priority and benefits of Korean patent application No. 10-2019-0118289, filed on Sep. 25, 2019, the disclosure of which is incorporated herein by reference in its entirety as part of the disclosure of this patent document.

TECHNICAL FIELD

The technology and implementations disclosed in this patent document generally relate to an electronic device including an image sensor.

BACKGROUND

An image sensor is a semiconductor device for capturing and converting optical images to electrical signals. The development of automotive, medical, computer, and communication industries is leading to an increase in the demand for high-performance image sensors in various devices such as smartphones, digital cameras, game consoles, Internet of Things (IoT), robots, surveillance cameras, medical microcameras, etc.

One common type of image sensing device is a charge coupled device (CCD), which has dominated the field of image sensors for a long time. Another common type of image sensing device is a complementary metal oxide semiconductor (CMOS) image sensing device. CCD image sensors have advantages over the CMOS image sensor in terms of noise characteristics and image quality. However, CMOS image sensors are now widely used due to certain advantages over the CCD counterparts, including, e.g., higher frame rates and shutter speed. In addition, CMOS image sensors and signal processing circuitry can be integrated into a single chip, making it possible to miniaturize electronic devices while achieving lower power consumption. In addition, using the CMOS fabrication technology can result in reduction in the production costs. Such characteristics of CMOS image sensors make these sensors better suited for implementations in mobile devices.

SUMMARY

The embodiments of the disclosed technology, among other features and benefits, relate to an image sensor that can be used to detect gas.

In an embodiment of the disclosed technology, an electronic device may include an image sensor including at least one grid structure that extends in rows and columns of a pixel array including a plurality of imaging pixels and is structured to separate the imaging pixels from one another to provide optical isolation between two adjacent imaging pixels, a grid shutter coupled to the grid structure and configured to allow a gas to enter the grid structure by opening a passage for the gas or block the gas from entering the grid structure by closing the passage in the grid structure, and a gas detection controller configured to identify the gas flowing into the grid structure based on an image that is acquired by the image sensor when the passage for the gas in the grid structure is opened to allow the gas to be present in the grid structure.

In another embodiment of the disclosed technology, an electronic device may include an image sensor including at least one grid structure disposed between color filters contiguous to each other and including a void space structured to receive and temporarily hold external gas, and a gas detection controller configured to identify the external gas flowing into the void space of the grid structure based on an image that is acquired by the image sensor in a situation in which the grid structure is holding the external gas in the void space.

In another embodiment of the disclosed technology, an electronic device may include an image sensor including at least one air grid that extends either in a row direction or in a column direction of a pixel array, a grid shutter configured to open or close the air grid, and a gas detection controller configured to determine external gas flowing into the air grid based on an image that is acquired by the image sensor in a situation in which the air grid is opened.

In another embodiment of the disclosed technology, an electronic device may include an image sensor including at least one air grid that is disposed between color filters contiguous to each other and temporarily receives external gas, and a gas detection controller configured to determine external gas flowing into the air grid based on an image that is acquired by the image sensor in a situation in which the air grid is opened.

BRIEF DESCRIPTION OF THE DRAWINGS

FIG. 10 is a table illustrating one example of a feature image map based on the gas detection method based on some embodiments of the disclosed technology.

DETAILED DESCRIPTION

Figure 1:
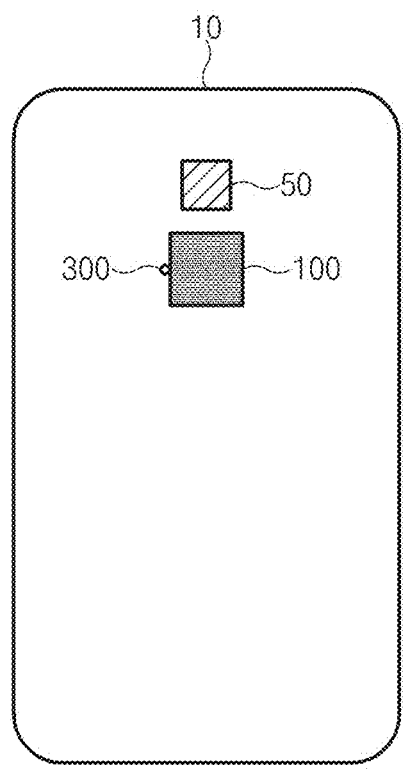
FIG. 1 is a block diagram illustrating an electronic device based on an embodiment of the disclosed technology.

FIG. 1 is a block diagram illustrating an electronic device 10 based on an embodiment of the disclosed technology.

In some implementations, the electronic device 10 based on various embodiments of the disclosed technology may be implemented as a smartphone, a tablet personal computer (PC), a mobile phone, a video phone, an electronic book (E-book) reader, a desktop PC, a laptop, a netbook computer, a workstation, a server, a personal digital assistant (PDA), a portable multimedia player (PMP), an MP3 player, a medical device, a camera, a wearable device, etc. Such a wearable device may include an accessory type device (e.g., watch, ring, bracelet, ankle bracelet, necklace, glasses, contact lenses), a head mounted device (HMD), a textile or clothing integral type device (e.g., electronic clothing), a body attachment type device (e.g., skin pad or tattoo), and a bio implantable circuit. In certain embodiments, the electronic device 10 may include a television, a digital video disk (DVD) player, an audio device, a refrigerator, an air-conditioner, a cleaner, an oven, a microwave oven, a washing machine, an air cleaner, a set-top box, a home automation control panel, a security control panel, a media box, a game console, an electronic dictionary, an electronic key, a camcorder, or an electronic frame.

In another embodiment, the electronic device 10 may include medical devices (e.g., various portable medical measurement devices (a blood sugar measurement device, a heartbeat measurement device, a blood pressure measurement device, and a body temperature measurement device), a magnetic resonance angiography (MRA) device, a magnetic resonance imaging (MRI) device, a computed tomography (CT) device, a scanning machine, and an ultrasonic device), a navigation device, a global navigation satellite system (GNSS), an event data recorder (EDR), a flight data recorder (FDR), a vehicle infotainment device, a ship electronic equipment (e.g., a ship navigation device, a gyro compass, etc.), avionics, a security device, a vehicle head unit, an industrial or home robot, a drone, an automatic teller's machine (ATM) of a financial institution, a point of sales (POS) of store, or Internet of things (IoT) devices (e.g., a bulb, various sensors, a sprinkler, a fire alarm, a thermostat, a street light, a toaster, an exercise device, a hot water tank, a heater, a boiler, etc.). In another embodiment, the electronic device 10 may be implemented as furniture, a portion of a building/structure or a vehicle, an electronic board, an electronic signature receiving device, a projector, or various measurement devices (e.g., water supply, electricity, gas, or electric wave measurement device). In another embodiment, the electronic device 10 may be implemented as a flexible device or may be combinations of two or more of the foregoing various devices.

The electronic device 10 based on various embodiments of the disclosed technology is not limited to the foregoing devices. In this document, a term 'user' may indicate either a person who uses the electronic device 10 or a device (e.g., an artificial intelligence electronic device) designed to use the electronic device 10.

By way of example, FIG. 1 illustrates the electronic device 10 as a smartphone, and it should be noted that the electronic device 10 can be any device that includes a light emitter 50, an image sensor 100, and a grid shutter 300 (e.g., at a rear surface of the electronic device 10).

In some embodiments of the disclosed technology, the light emitter 50 may be an apparatus for emitting light having a specific brightness range, a specific wavelength range, and/or a specific directivity range, for example, to the outside of the electronic device 10, and may include at least one light emitting diode (LED). For example, the LED may include at least one of a red-green-blue (RGB) LED, a white LED, an infrared (IR) LED, or an ultraviolet (UV) LED.

The image sensor 100 may convert light received from a target object through a lens assembly into an electric signal to acquire an image corresponding to the target object. In some embodiments of the disclosed technology, the image sensor 100 may include a single image sensor selected from among a plurality of image sensors having different attributes, for example, an RGB sensor, a black-and-white (BW) sensor, an IR sensor, and an UV sensor, may include a plurality of image sensors having the same attributes, or may include a plurality of image sensors having different attributes. Each image sensor contained in the image sensor 100 may be implemented as a complementary metal oxide semiconductor (CMOS) sensor. In this case, the lens assembly may collect light emitted from the target object to be photographed. The lens assembly may include a single lens or a plurality of lenses arranged along one optical axis.

The grid shutter 300 may be structured to allow gas present outside the electronic device 10 to be introduced into the image sensor 100 by opening an aperture, and may limit the passage of the gas present outside the electronic device into the image sensor 100 by closing the aperture. In some implementations, the grid shutter 300 may be disposed adjacent to the image sensor 100, such that the grid shutter 300 may open or close a passage through which gas can be introduced or discharged. The shape and placement/position of the grid shutter 300 are not limited to those of FIG. 1. In another embodiment, the grid shutter 300 may also be designed to be visually identified by naked eyes of a user located outside the electronic device 10.

Figure 2:
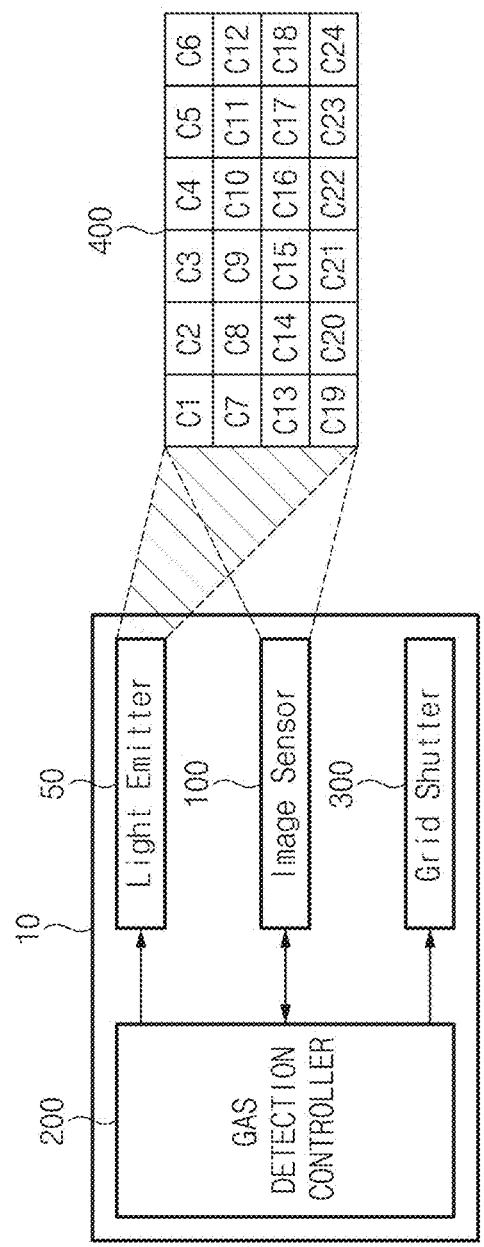
FIG. 2 is a block diagram illustrating constituent elements of the electronic device that are related to a gas detection operation based on an embodiment of the disclosed technology.

FIG. 2 is a block diagram illustrating constituent elements of the electronic device 10 that are related to a gas detection operation based on an embodiment of the disclosed technology.

In some implementations, the electronic device 10 may include a light emitter 50, an image sensor, a gas detection controller 200, and a grid shutter 300.

The light emitter 50 may be turned on or off under control of the gas detection controller 200. The light emitter 50 may emit light of a predetermined brightness, a predetermined wavelength, and a predetermined directivity to the outside of the electronic device 10. Although FIG. 2 illustrates the light emitter 50 as emitting light toward a standard color chart 400 for a gas detection operation, the gas detection operation may also be carried out without using the standard color chart 400 based on another embodiment. In this case, the light emitter 50 may emit light toward any target object rather than the standard color chart 400. The standard color chart 400 may include a plurality of representative colors. For example, the standard color chart 400 may be based on a pantone color system, a Japanese color system (DIC; Dianippon Ink & Chemicals), and a color coordinate system (COS). In addition, although the standard color chart 400 may include a plurality of colors C1 to C24 arranged in a (4×6) matrix as shown in FIG. 2, types of colors, the number of colors, and arrangement of colors contained in the standard color chart 400 may vary depending on applications.

The image sensor 100 may acquire an image corresponding to the target object under control of the gas detection controller 200. The gas detection controller 200 may activate or deactivate the gas detection operation according to a user request or a predetermined internal interrupt signal. In the case where the gas detection operation is deactivated, the image sensor 100 may acquire a normal image (e.g., color image, depth image). In the case where the gas detection operation is activated, the image sensor 100 may acquire the image corresponding to the target object for determining an external gas. The target object may be a standard color chart 400, or may be any object that can be used to perform the gas detection operation by differentiating its image or color captured by the image sensor 100 according to the gas detected. In addition, the image sensor 100 may provide the acquired image to the gas detection controller 200 to perform the gas detection operation. In some implementations, the image provided to the gas detection controller 200 may be analog pixel data or digital pixel data acquired by converting the analog pixel data to the digital pixel data (see FIG. 3). In another embodiment, the image provided to the gas detection controller 200 may be pixel data acquired by performing image processing on the pixel data. For example, the image processing may include depth-map generation, three-dimensional (3D) modeling, panoramic generation, characteristic point extraction, image synthesis, or image compensation (e.g., noise reduction, resolution adjustment, brightness adjustment, blurring, sharpening, or softening). To this end, the electronic device 10 may further include an image signal processor (not shown).

The image signal processor may perform image processing on images acquired through the image sensor 100, or may perform image processing on images stored in a separate memory. In some embodiments of the disclosed technology, the image signal processor may be included in at least some parts of a main processor (e.g., an application processor) of the electronic device 10, or may be implemented as a separate processor operated independently from the main processor. In another embodiment, the image signal processor may be integrated with the gas detection controller 200. In this case, the gas detection controller 200 may include the image signal processor (not shown) and the gas detection controller 200. In another implementation, the image signal processor may additionally perform functions of the gas detection controller 200.

The grid shutter 300 may control the passage of gas existing outside the electronic device 10 such that whether to allow the gas to move into the image sensor 100 is determined based on control signals provided by the gas detection controller 200. To this end, one side of the grid shutter 300 may be coupled to an optical isolation structure which is structured to include an air grid structure of hollow grid structures included in the image sensor 100, and the other side of the grid shutter 300 may be structured to include one or more gas passages for receiving gas from outside the electronic device 10 (e.g., exterior surfaces of the electronic device 10). The grid shutter 300 may be engaged to the one or more gas passages to open or close a gas inlet passage disposed between the image sensor 100 and the external part of the electronic device 10. In other words, the grid shutter 300 may open or close the air grid structure of the image sensor 100.

The gas detection controller 200 may control constituent elements 50, 100, 300 of the electronic device 10 so as to perform the gas detection operation. Upon commencement of the gas detection operation, the gas detection controller 200 may control the grid shutter 300 to open the gas inlet passage such that external gas can be introduced from outside into inside the image sensor 100. The gas detection controller 200 may control the light emitter 50 to emit light toward the target object. In addition, the gas detection controller 200 may control the image sensor 100 to acquire an image corresponding to the target object. The gas detection controller 200 may generate information about gas that exists in the external part of the electronic device 10 based on the target object image acquired while the air grid structure is opened by the grid shutter 300. Such gas information may include information about the type and concentration of the gas. A method for controlling the gas detection controller 200 to generate gas information will be described later with reference to FIGS. 9 to 11. Gas information generated by the gas detection controller 200 may be stored in a memory (not shown), or may be displayed for each user through a display (not shown).

Figure 3:
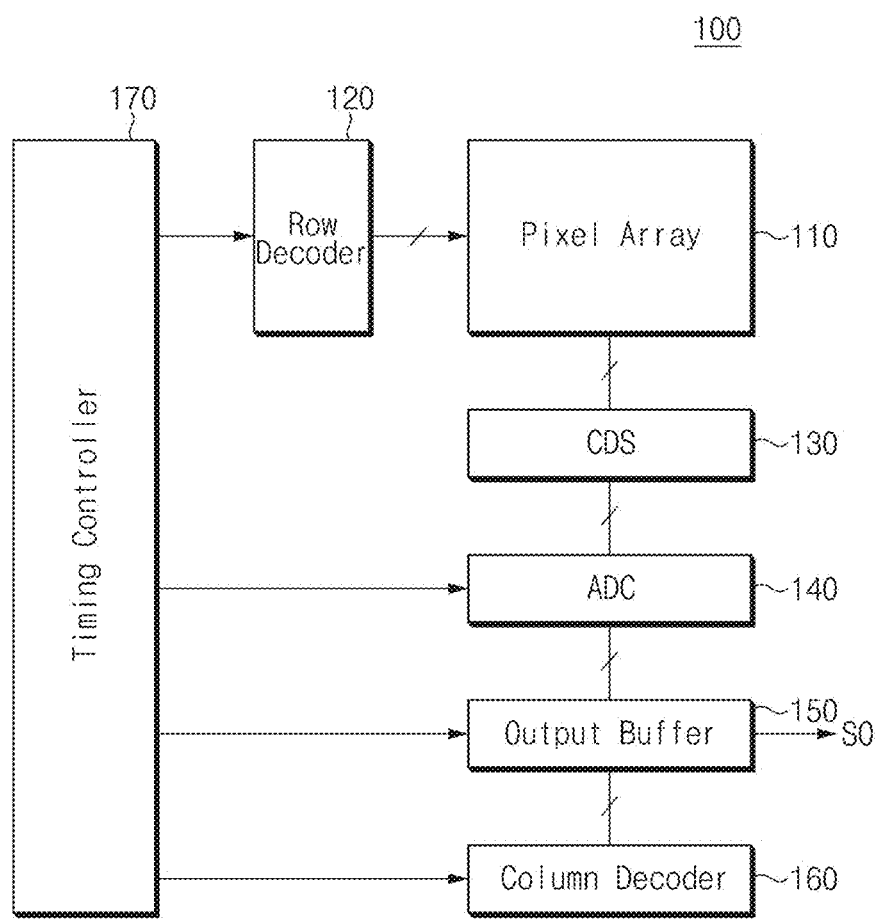
FIG. 3 is a block diagram illustrating an image sensor shown in FIG. 2 based on some embodiments of the disclosed technology.
Figure 4:
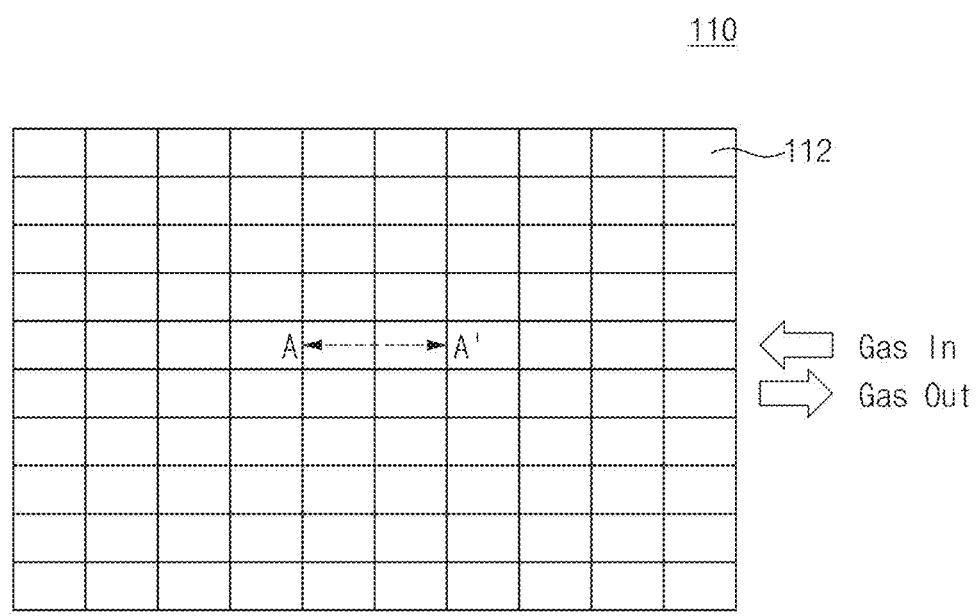
FIG. 4 is a detailed schematic diagram illustrating a pixel array shown in FIG. 3 based on some embodiments of the disclosed technology.

FIG. 3 is a block diagram illustrating an example of the image sensor 100 based on some embodiments of the disclosed technology. FIG. 4 is a detailed schematic diagram illustrating a pixel array shown in FIG. 3 based on some embodiments of the disclosed technology.

Referring to FIG. 3, the image sensor 100 may include a pixel array 110, a row decoder 120, a correlated double sampling (CDS) circuit 130, an analog-to-digital converter (ADC) 140, an output buffer 150, a column decoder 160, and a timing controller 170. In this case, the above-mentioned constituent elements of the image sensor 100 are merely examples, and one or more constituent elements may be added to or omitted from the image sensor 100 as necessary.

The pixel array 110 may include a plurality of unit pixels arranged in a two-dimensional (2D) array. In an implementation, the plurality of unit pixels may be arranged such that each unit pixel has its own dedicated driver circuits. In another implementation, the pixel array 110 may have a shared pixel structure where at least two unit pixels share at least one common driver circuit in converting an optical signal (or incident light) into an electrical signal. The pixel array 110 may receive operating signals including a row selection signal, a pixel reset signal, and a transmission (Tx) signal from the row decoder 120, and may be operated by the drive signal received from the row decoder 120.

As shown in FIG. 4, an example of the pixel array 110 may include a plurality of unit pixels 112 arranged in a matrix shape including a plurality of rows and a plurality of columns. By way of example, the unit pixels 112 arranged in a (10×10) matrix are illustrated in FIG. 4 for convenience of description, and it should be noted that the number of rows and the number of columns in the pixel array 110 may vary.

The unit pixels 112 may respectively include color filters, and unit air grid structures may be disposed between color filters of neighboring unit pixels to prevent optical crosstalk. In an implementation, the unit air grid structures may be connected each other to form an integrated air grid structure. In another implementation where the pixel array 110 is divided into two or more regions (e.g., pixels belonging to the first to fifth rows and pixels belonging to the sixth to tenth rows), the unit air grid structures are connected to each other to form two or more integrated air grid structures such that each region has its own integrated air grid structure. Therefore, the air grid may be formed in a mesh-shaped pattern.

In some implementations, the grid shutter 300 shown in FIG. 2 may be coupled to the air grid structure to open or close the gas inlet passage. In one example, the grid shutter 300 may open the gas inlet passage in a manner that external gas of the electronic device 10 can enter (gas-in) or exit (gas-out) the air grid, and may close the gas inlet passage in a manner that external gas of the electronic device 10 is prevented from entering the air grid.

In some implementations, the grid shutter 300 is connected to the air grid of the pixel array 110 such that at least one opening portion of the integrated air grid structure is connected to the grid shutter 300. The at least one opening portion may be disposed at one side (i.e., upper, lower, left, or right side) of the integrated air grid structure, or may be disposed at a plurality of side surfaces of the integrated air grid structure. In addition, the opening portion may be disposed at the side surface of each unit pixel, or may be disposed at a top surface of each unit pixel.

As shown in FIG. 3, the row decoder 120 may be used to select desired rows of the pixel array 110 based on control signals generated by the timing controller 170. In some implementations, in selecting rows from the pixel array 110, the row decoder 120 may generate a row selection signal to select at least one of a plurality of rows. The row decoder 120 may sequentially enable a pixel reset signal for resetting pixels corresponding to at least one selected row, and a transmission (Tx) signal for transmitting electrical signals generated by the selected pixels. As a result, an analog-type reference signal and an image signal that are generated from each pixel of the selected row may be sequentially transmitted to the CDS circuit 130. In this case, the reference signal and the image signal may be collectively called a pixel signal.

CMOS image sensors may use the correlated double sampling (CDS) to remove an undesired offset value of pixels by sampling a pixel signal twice to remove the difference between these two samples. In one example, the correlated double sampling (CDS) may remove the undesired offset value of pixels by comparing pixel output voltages obtained before and after a light signal is incident on the pixels so that only pixel output voltages based on the incident light can be measured. In some embodiments of the disclosed technology, the CDS circuit 130 may sequentially sample and hold the reference signal and the image signal that are transferred from the pixel array 110 to each of the plurality of column lines. That is, the CDS circuit 130 may sample and hold levels of the reference signal and the image signal that correspond to each column of the pixel array 110.

The CDS circuit 130 may transmit a correlated double sampling (CDS) signal corresponding to the reference signal and the image signal for each column to the ADC 140 upon receiving a control signal from the timing controller 170.

The ADC block is used to convert analog CDS signals to digital signals. Examples of the ADC 140 may include a ramp-compare type ADC where the analog pixel signal is compared with a reference signal such as a ramp signal that ramps up or down and a timer counts until a voltage of the ramp signal matches the analog pixel signal. In some embodiments of the disclosed technology, the ADC 140 may receive the CDS signal for each column from the CDS circuit 130, may convert the received CDS signal into a digital signal, and may thus output the digital signal. In some implementations, the ADC 140 samples an input signal (e.g., pixel signal) multiple times using the reference signal and analog-to-digital convert the sampled input signals by counting the number of clock pulses until crossing points. The ADC 140 may perform counting and calculation operations based on the CDS signal for each column and a ramp signal received from the timing controller 170, such that the ADC 140 may generate digital image data from which noise (e.g., unique reset noise for each pixel) corresponding to each column is removed.

The ADC 140 may include a plurality of column counters corresponding to respective columns of the pixel array 110, and may convert the CDS signal for each column into a digital signal using the column counters, forming image data. In another embodiment, the ADC 140 may include a single global counter, and may convert a CDS signal corresponding to each column into a digital signal using a global code received from the global counter.

The output buffer 150 may be used to receive image data for each column received from the ADC 140. The output buffer 150 may capture the received image data and output the captured image data. The output buffer 150 may temporarily store image data that is output from the ADC 140 upon receiving a control signal from the timing controller 170. The output buffer 150 may operate as an interface configured to compensate for data rate difference or transmission (Tx) speed difference between the image sensor 100 and another device coupled to the image sensor 100.

The column decoder 160 may be used to select a column of the output buffer 150 upon receiving a control signal from the timing controller 170, and may sequentially output the temporarily stored image data to the output buffer 150. In some implementations, the column decoder 160 may receive an address signal from the timing controller 170, may generate a column selection signal based on the received address signal, and may select a column of the output buffer 150 to output image data as an output signal S0 from the selected column of the output buffer 150.

The timing controller 170 may control the row decoder 120, the ADC 140, the output buffer 150, and the column decoder 160.

The timing controller 170 may transmit a clock signal for operating or synchronizing the constituent elements of the image sensor 100, a control signal for timing control, and address signals for selection of a row or column to the row decoder 120, the column decoder 160, the ADC 140, and the output buffer 150. In some embodiments of the disclosed technology, the timing controller 170 may include a logic control circuit, a phase locked loop (PLL) circuit, a timing control circuit, a communication interface circuit, etc.

Figure 5:
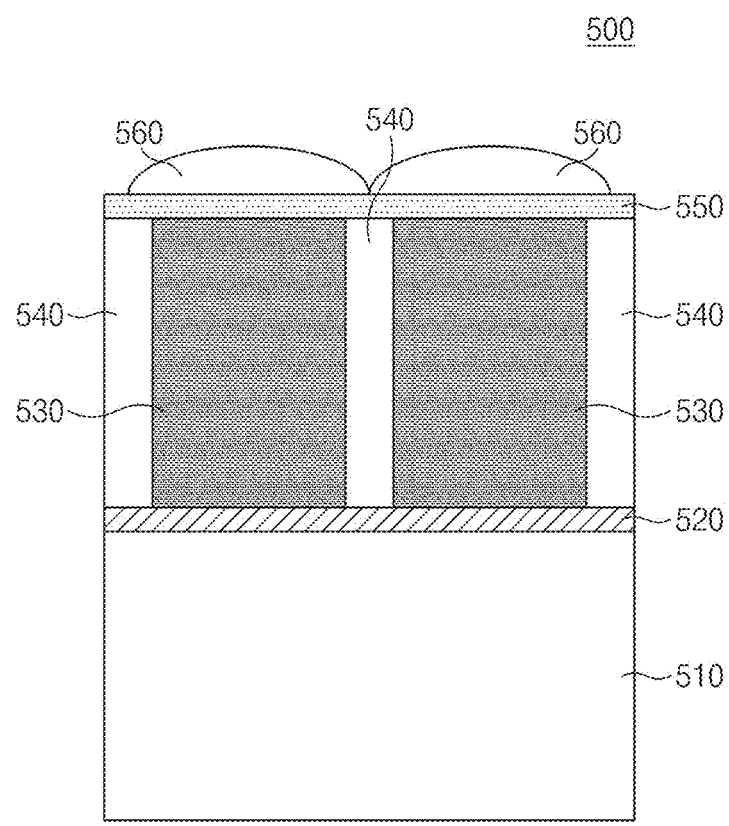
FIG. 5 is a cross-sectional view illustrating one example of the pixel array shown in FIG. 4 based on some embodiments of the disclosed technology.

FIG. 5 is a cross-sectional view illustrating one example of the pixel array 110 shown in FIG. 4 based on some embodiments of the disclosed technology.

Referring to FIG. 5, a cross-sectional view 500 of the pixel array 110 may represent cross-sections of the contiguous unit pixels taken along the line A-A' shown in FIG. 4. Although FIG. 5 illustrates a cross-sectional view of only two unit pixels for convenience of description, other unit pixels contained in the pixel array 110 may be substantially identical in structure to each other. In another embodiment, the structure corresponding to the cross-sectional view 500 of the pixel array 110 may be applied only to some unit pixels rather than all unit pixels included in the pixel array 110.

The cross-sectional view 500 of the pixel array 110 may include a substrate 510, an anti-reflection layer 520, a color filter 530, an air grid 540, an over-coating layer 550, and a microlens 560.

The substrate 510 may include a top surface and a bottom surface facing each other. By way of example, the top surface of the substrate 510 can be defined as a front side and the bottom surface of the substrate 510 can be defined as a back side. In some implementations, the substrate 510 may be a P-type or N-type bulk substrate, may be a P-type bulk substrate in which a P-type or N-type epitaxial layer is grown, or may be an N-type bulk substrate in which a P-type or N-type epitaxial layer is grown. The substrate 510 may include a photodiode that accumulates photocharges corresponding to the amount of incident light in an inner region thereof, a plurality of doped regions needed to operate the unit pixels, a device isolation layer for isolating the unit pixels from each other. As an example, the photodiode may be formed as an N-type doped region through ion implantation of N-type ions.

The anti-reflection layer 520 may compensate for a difference in refractive index between the color filter 530 and the substrate 510, such that the anti-reflection layer 520 may allow light having passed through the color filter 530 to be effectively incident into the substrate 510. In one example, the anti-reflection layer 520 may be formed of silicon oxide.

The color filter 530 may be formed over the anti-reflection layer 520, and may selectively allow a light signal (e.g., red light, green light, blue light, magenta light, yellow light, cyan light, or the like) having a specific wavelength to pass while blocking the other wavelengths.

The air grid 540 may be disposed between the contiguous color filters 530 to prevent occurrence of optical crosstalk between the contiguous color filters 530. Although FIG. 5 illustrates the height of the air grid 540 from the top surface of the anti-reflection layer 520 as being identical to the height of the color filter 530 for convenience of description, the height of the air grid 540 may be higher or lower than the height of the color filter 530 as needed. The air grid 540 may be coupled to or blocked from the external part of the electronic device 10 through the grid shutter 300, and may temporarily receive or discharge external gas introduced through the grid shutter 300.

The air grid 540 may include an air region, a capping film, and a supporting film.

The air region may be filled with a material having a relatively low refractive index such as air (e.g., '1'). In another embodiment, a material (e.g., tungsten) having a high light absorption rate may be additionally disposed below the air region.

The capping film may be formed to surround the entirety of the air region, and the shape of the air region may be defined by the capping film.

The supporting film may be formed to surround the capping film. The capping film may be formed as thin as possible in a manner that gas existing in the air region can be easily discharged outside in a fabrication process of the air grid. Here, the supporting film may be disposed to surround the entire capping film in a manner that the shape of the capping film having a thin thickness can be well maintained.

The refractive index of each of the capping film and the supporting film may be higher than the refractive index (e.g., '1') of the air region, and may also be lower than the refractive index (e.g., 1.6-1.7) of the color filter 530. In accordance with one embodiment, each of the capping film and the supporting film may include an ultra low temperature oxide (ULTO) film such as a silicon oxide film ($SiO_2$).

As external gas is introduced into the air region according to the operation of the grid shutter 300, the refractive index of the air region may be changed. For example, although the refractive index of the air region may be set to '1' before external gas is introduced into the air region (i.e., at ordinary times), the refractive index of the air region may become higher when the external gas is introduced in to the air region and this refractive index varies depending on the type and concentration of the external gas as the external gas is introduced into the air region. The change in refractive index of the air region may change a route of light passing through the color filter 530, and the amount of photocharges accumulated in the photodiode of the substrate 510 may be changed due to the changes in the route of light.

The over-coating layer 550 may be disposed over the color filter 530 and the air grid 540, and may prevent diffused reflection of incident light received from the outside, thereby suppressing flare characteristics. In addition, the over-coating layer 550 may compensate for a step difference between the color filter 530 and the air grid 540, so that the over-coating layer 550 may allow the microlens 560 to have a constant height.

The microlens 560 may be formed over the over-coating layer 550, and may increase light gathering power of incident light, resulting in increased light reception (Rx) efficiency of the photodiode of the substrate 510.

Figure 6:
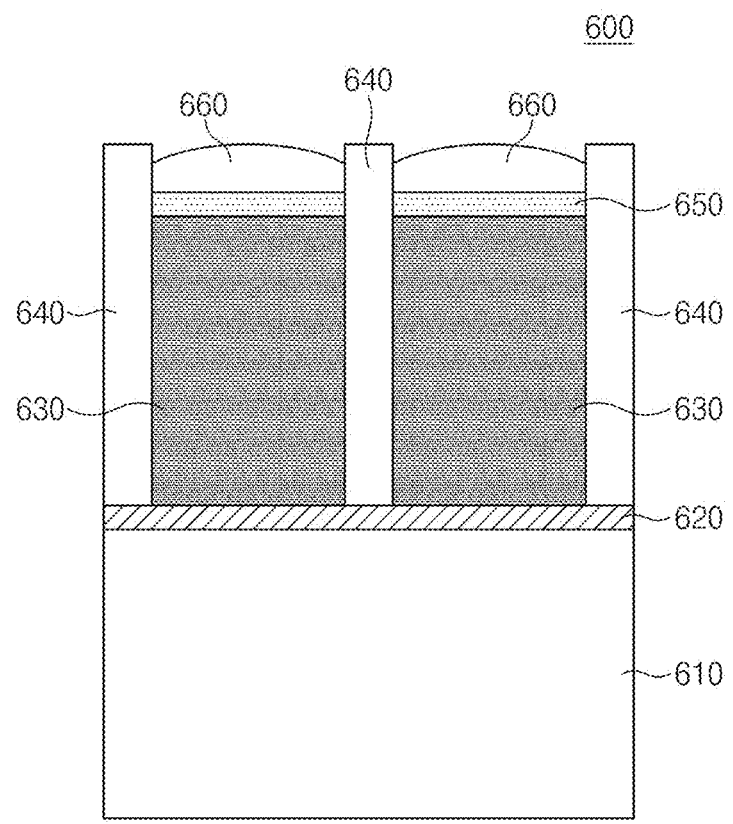
FIG. 6 is a cross-sectional view illustrating another example of the pixel array shown in FIG. 4 based on some embodiments of the disclosed technology.

FIG. 6 is a cross-sectional view illustrating another example of the pixel array 110 shown in FIG. 4 based on the disclosed technology.

Referring to FIG. 6, a cross-sectional view 600 of the pixel array 110 may represent cross-sections of the contiguous unit pixels taken along the line A-A' shown in FIG. 4. In this case, although FIG. 6 illustrates a cross-sectional view of only two unit pixels for convenience of description, other unit pixels contained in the pixel array 110 may be substantially identical in structure to each other. In another embodiment, the structure corresponding to the cross-sectional view 600 of the pixel array 110 may be applied only to some unit pixels rather than all unit pixels included in the pixel array 110.

The cross-sectional view 600 of the pixel array 110 may include a substrate 610, an anti-reflection layer 620, a color filter 630, an air grid 640, an over-coating layer 650, and a microlens 660. Except for some differences between constituent elements of FIG. 5 and FIG. 6, the above-mentioned constituent elements 610-660 contained in the cross-sectional view 600 of the pixel array 110 shown in FIG. 6 may be substantially identical in structure and material to those of the respective constituent elements 510-560 contained in the cross-sectional view 500 of the pixel array 110 shown in FIG. 5.

Unlike the air grid 540 shown in FIG. 5, the air grid 640 shown in FIG. 6 may be configured in a manner that the height of the air grid 640 from the anti-reflection layer 620 is higher than each of the over-coating layer 650 and the color filter 630, and the air grid 640 may be formed to protrude outward from the pixel array 110 at a position located between the contiguous microlenses 660. The air grid 640 may more effectively prevent occurrence of optical crosstalk between the contiguous unit pixels, and an opening portion needed for connection to the grid shutter 300 may be formed at a top surface of the unit pixel due to the air grid 640 protruding outward.

Figure 7:
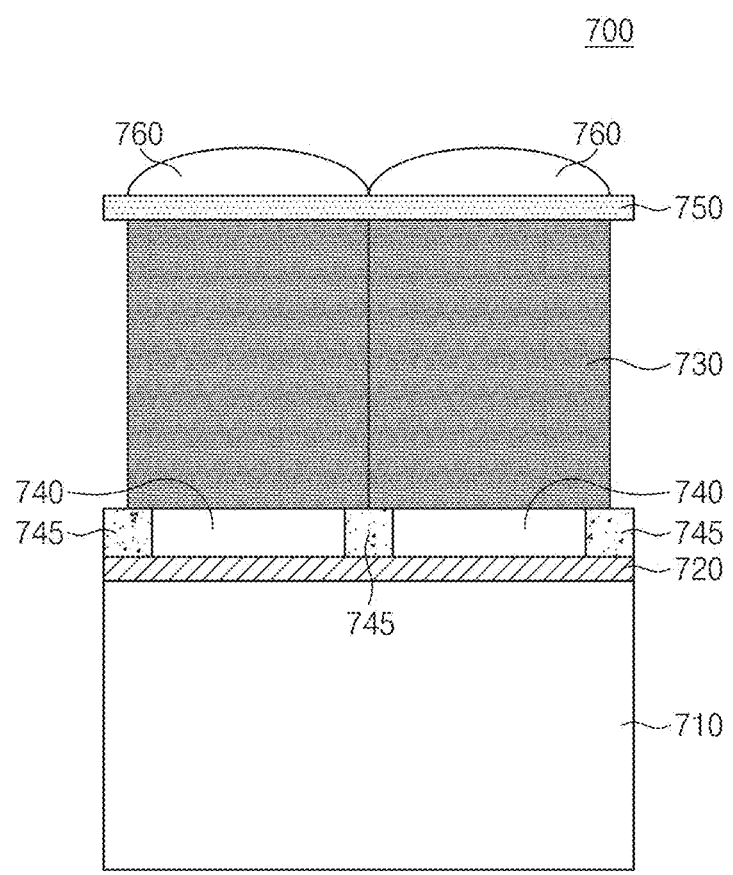
FIG. 7 is a cross-sectional view illustrating another example of the pixel array shown in FIG. 4 based on some embodiments of the disclosed technology.

FIG. 7 is a cross-sectional view illustrating another example of the pixel array 110 shown in FIG. 4 based on some embodiments of the disclosed technology.

Referring to FIG. 7, a cross-sectional view 700 of the pixel array 110 may represent cross-sections of the contiguous unit pixels taken along the line A-A' shown in FIG. 4. Although FIG. 7 illustrates a cross-sectional view of only two unit pixels for convenience of description, other unit pixels contained in the pixel array 110 may be substantially identical in structure to each other. In another embodiment, the structure corresponding to the cross-sectional view 700 of the pixel array 110 may be applied only to some unit pixels rather than all unit pixels included in the pixel array 110.

The cross-sectional view 700 of the pixel array 110 may include a substrate 710, an anti-reflection layer 720, a color filter 730, an air grid 740, a grid isolation layer 745, an over-coating layer 750, and a microlens 760. Except for some differences between constituent elements of FIG. 7 and FIG. 5, the above-mentioned constituent elements 710-760 contained in the cross-sectional view 700 of the pixel array 110 shown in FIG. 7 may be substantially identical in structure and material to those of the respective constituent elements 510-560 contained in the cross-sectional view 500 of the pixel array 110 shown in FIG. 5, and as such redundant matters thereof will herein be omitted for brevity.

Unlike the air grid 540 shown in FIG. 5, the air grid 740 shown in FIG. 7 may be disposed below the color filter 730 rather than between the contiguous color filters 730. In another embodiment, the air grid 740 and an additional air grid (not shown) disposed between the contiguous color filters 730 in the same manner as in the air grid 540 of FIG. 5 may also be used.

As the air grid 740 is disposed under the color filter 730 in the example shown in FIG. 7, the changes in the route of light beams passing through the color filter 730 due to external gas introduced into the air region can be more sensitive as compared to the structure in which the air grid is disposed between the contiguous color filters 730. Because the air grid 740 is disposed at the route of light beams directly passing through the color filter 730, gas detection performance for detecting such external gas can be improved.

On the other hand, a grid isolation layer 745 may be disposed between the air grids 740 contiguous to each other. The grid isolation layer 745 may optically isolate (or separate) the contiguous air grids 740 from each other. The grid isolation layer 745 may be formed of the same material as the supporting film of the air grid 740, and may be formed integrally with the supporting film of the air grid 740. Alternatively, the grid isolation layer 745 may be formed through a separate gap-fill process.

Figure 8:
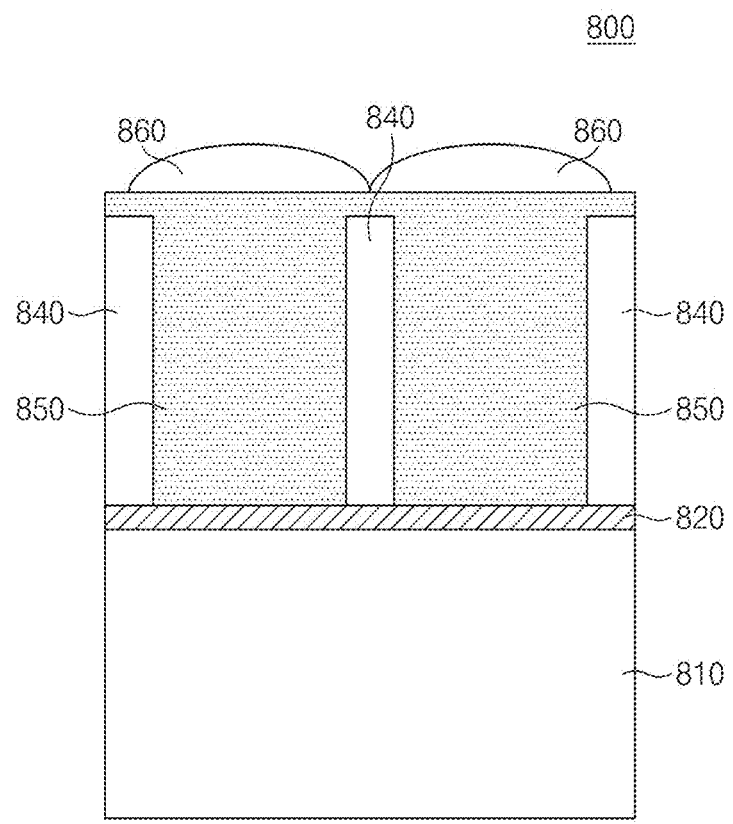
FIG. 8 is a cross-sectional view illustrating another example of the pixel array shown in FIG. 4 based on some embodiments of the disclosed technology.

FIG. 8 is a cross-sectional view illustrating another example of the pixel array 110 shown in FIG. 4 based on the disclosed technology.

Referring to FIG. 8, a cross-sectional view 800 of the pixel array 110 may represent cross-sections of the contiguous unit pixels taken along the line A-A' shown in FIG. 4. Although FIG. 8 exemplarily illustrates a cross-sectional view of only two unit pixels for convenience of description, other unit pixels contained in the pixel array 110 may be substantially identical in structure to each other. In another embodiment, the structure corresponding to the cross-sectional view 800 of the pixel array 110 may be applied only to some unit pixels rather than all unit pixels included in the pixel array 110.

The cross-sectional view 800 of the pixel array 110 may include a substrate 810, an anti-reflection layer 820, a color filter 830, an air grid 840, an over-coating layer 850, and a microlens 860. Except for some differences between constituent elements of FIG. 8 and FIG. 5, the above-mentioned constituent elements 810-860 contained in the cross-sectional view 800 of the pixel array 110 shown in FIG. 8 may be substantially identical in structure and material to those of the respective constituent elements 510-560 contained in the cross-sectional view 500 of the pixel array 110 shown in FIG. 5.

The cross-sectional view 800 of the pixel array 110 does not to include the color filter, unlike the cross-sectional view 500 of FIG. 5. That is, the position where the color filter 530 otherwise would have been disposed may also be filled with the over-coating layer 850.

If the over-coating layer 850 is formed of a material that allows all light in the visible spectrum to pass through, the pixel signal of each unit pixel may represent brightness of incident light. Here, image sensors including such unit pixels may be referred to as a black white (BW) sensor.

If the over-coating layer 850 is formed of a material that allows light of the infrared (IR) wavelength band to pass through, the pixel signal of each unit pixel may represent intensity of infrared (IR) light. Here, image sensors including such unit pixels may be referred to as an IR sensor.

The changes to the route of light of the infrared (IR) wavelength band that passes through the over-coating layer 850 may be more sensitive to external gas introduced into the air region because gas has a resonance wavelength in the infrared (IR) wavelength band, resulting in improvement in gas detection performance for detecting external gas.

Figure 9:
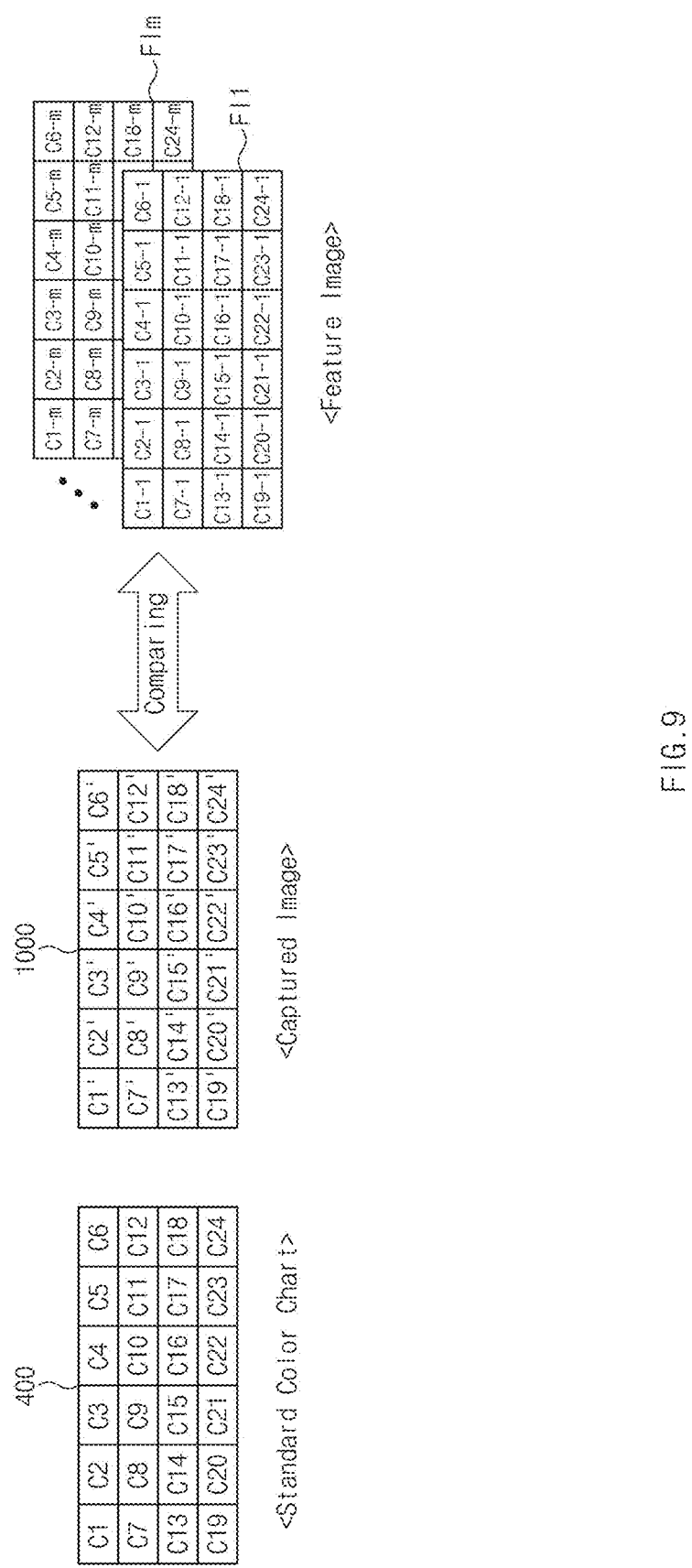
FIG. 9 is a diagram illustrating a method for controlling a gas detection controller shown in FIG. 2 to sense gas based on some embodiments of the disclosed technology.

FIG. 9 is a diagram illustrating a method for controlling a gas detection controller shown in FIG. 2 to sense gas based on some embodiments of the disclosed technology. FIG. 10 is a table illustrating one example of a feature image map based on the gas detection method in some embodiments of the disclosed technology.

Referring to FIG. 9, as previously described in FIG. 2, the image sensor 100 may acquire the image acquired when the standard color chart 400 is photographed under control of the gas detection controller 200.

In some implementations, since external gas is introduced into the air region of the air grid contained in the image sensor 100 by opening the grid shutter 300, the refractive index of the air region is changed according to the type and concentration of the external gas, and the captured image 1000 acquired by photographing of the standard color chart 400 may be different from the standard color chart 400 due to the changed refractive index. In this case, the color change of the captured image 1000 with respect to the standard color chart 400 due to external gas flowing into the air region may depend on the colors C1-C24 contained in the standard color chart 400. In addition, the color change of the captured image 1000 with respect to the standard color chart 400 due to the inflow of specific external gas may have constant shaping characteristics. Such shaping characteristics may be represented by a feature image corresponding to specific external gas. The feature image FI1-FIm (where 'm' is an integer of 2 or more) corresponding to each external gas may be acquired experimentally, and the gas detection controller 200 may maintain a feature image map in which each feature image FI1-FIm corresponding to each external gas is formed in a table.

Referring to FIG. 10, one example of the feature image map is illustrated. As can be seen from the feature image map of FIG. 10, when each external gas Gas1-Gasm (where 'm' is an integer of 2 or more) is introduced into the air region, the captured image 1000 about the standard color chart 400 is experimentally acquired, so that the captured images 1000 can be constructed for individual colors C1-C24. For example, in a situation in which the methane gas ($CH_4$) is introduced into the air region and the captured image 100 about the standard color chart 400 is then experimentally acquired, the feature image of the methane gas ($CH_4$) may include values indicating the above-mentioned experimentally acquired results for each of colors C1-C24.

In this case, the above operation of experimentally acquiring the resultant values may indicate that the captured image 100 for specific external gas is repeatedly acquired, and an average of a feature value for each of colors C1-C24 of the captured images 1000 is determined as feature images FI1-FIm of specific external gas. The feature value for each of colors C1-C24 may include information about intensity and saturation.

Although FIG. 10 illustrates feature values for each of colors C1-C24 as determined within the range of 0 to 255 (256 colors in 8-bit color graphics) for convenience of description, the scope of the disclosed technology is not limited thereto.

The gas detection controller 200 may compare the captured image 1000 acquired from the current image sensor 100 with a plurality of feature images FI1-FIm included in the feature image map, may decide any one of the feature images FI1-FIm based on the result of comparison, and may identify the gas corresponding to the decided feature image as the external gas flowing into the air region of the current image sensor 100.

In this case, the comparing of the captured image 1000 with the plurality of feature images FI1~FIm may include calculating a deviation between the feature value of the captured image 1000 for each color C1-C24 and the feature value of each feature image FI1-FIm for each color C1-C24, and calculating the sum of deviations for each of the feature images FI1-FIm and determining one feature image having the lowest sum of calculated deviations. The above-mentioned comparison scheme is disclosed only for illustrative purposes, and various schemes for determining similarity between the captured image 1000 and each of the feature images FI1-FIm may be used based on some embodiments of the disclosed technology.

Figure 11:
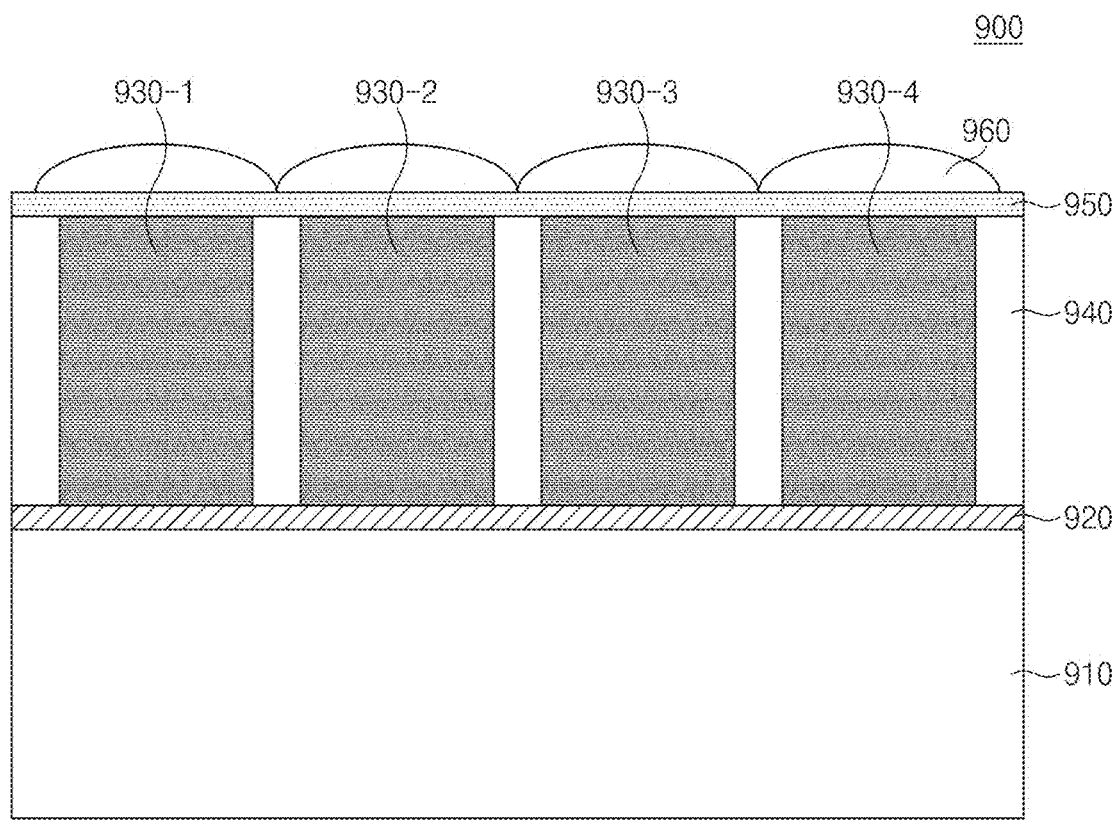
FIG. 11 is a cross-sectional view illustrating another example of the pixel array shown in FIG. 4 based on some embodiments of the disclosed technology.

FIG. 11 is a cross-sectional view illustrating another example of the pixel array shown in FIG. 4 based on the disclosed technology.

Referring to FIG. 11, the cross-sectional view 900 of the pixel array 110 may represent cross-sections of the contiguous unit pixels taken along a specific column (e.g., the outermost column) of the pixel array shown in FIG. 4. Although FIG. 11 illustrates a cross-sectional view of only four unit pixels for convenience of description, other unit pixels contained in the specific column may also be substantially identical in structure to each other. In another embodiment, the structure corresponding to the cross-sectional view 900 may also be applied to unit pixels contained either in a specific row or in at least two columns, rather than applied to the other unit pixels contained in the specific column.

The cross-sectional view 900 of the pixel array 110 may include a substrate 910, an anti-reflection layer 920, a plurality of spectral filters 930-1 to 930-4, an air grid 940, an over-coating layer 950, and a microlens 960. Except for some differences between constituent elements of FIG. 11 and FIG. 5, the above-mentioned constituent elements 910-960 contained in the cross-sectional view 900 of the pixel array 110 shown in FIG. 11 may be substantially identical in structure and material to those of the respective constituent elements 510-560 contained in the cross-sectional view 500 of the pixel array 110 shown in FIG. 5, and as such redundant matters thereof will herein be omitted for brevity.

Each of the spectral filters 930-1 to 930-4 may allow only a predetermined wavelength band to pass therethrough, and the wavelength bands respectively passing through the spectral filters 930-1 to 930-4 may be different from each other. In more detail, the spectral filters through which different wavelength bands can pass may be arranged along a specific column of the pixel array 110, and the unit pixels arranged along the specific column may construct a hyper spectral sensor that has a resolution corresponding to a specific value acquired when a total wavelength range is divided by the number (e.g., 1000) of spectral filters.

In other words, the image acquired from the unit pixels arranged along the specific column may be a spectral image representing spectral characteristics. In this case, the spectral image in a situation in which no external gas is introduced into the air region may be a reference spectral image, and the reference spectral image may be prestored in the gas detection controller 200 to be used during the operation of the grid shutter 300.

Since external gas is introduced into the air region of the air grid contained in the image sensor 100 by opening the grid shutter 300, the refractive index of the air region is changed based on the type and concentration of the external gas, and the spectral image acquired from the unit pixels arranged along the specific column may become different from the reference spectral image due to the changed refractive index. In this case, the change in spectral image affected by external gas flowing into the air region may be changed according to individual wavelengths. In addition, the change in spectral image affected by inflow of specific external gas may have constant shaping characteristics. Such shaping characteristics may be represented by a feature spectral image corresponding to specific external gas. The feature image FI1-FIm (where 'm' is an integer of 2 or more) corresponding to each external gas may be acquired experimentally, and the gas detection controller 200 may maintain a feature image map in which each feature image FI1-FIm corresponding to each external gas is formed in a table shape. The feature spectral image corresponding to each external gas may be acquired experimentally, and the gas detection controller 200 may prestore a feature spectral image map in which feature spectral images for each external gas are formed in a table shape.

In this case, the feature spectral image may include the amount of change with respect to a reference spectral image for each wavelength.

The gas detection controller 200 may compare an image (hereinafter referred to as a differential spectral image) corresponding to the result of calculation between the captured spectral image acquired from the current image sensor 100 and the reference spectral image, with a plurality of feature spectral images contained in the feature spectral image map, may decide any one of the plurality of feature spectral images based on the result of comparison, and may identify the gas corresponding to the decided feature spectral image as the gas flowing into the air region of the current image sensor 100.

In some implementations, the comparing of the differential spectral image with the plurality of feature spectral images may include calculating a deviation between the value of the differential spectral image for each wavelength and the value of each feature spectral image for each wavelength, and calculating the sum of deviations for each of the feature spectral images and determining one feature spectral image having the lowest sum of calculated deviations. The above-mentioned comparison scheme is disclosed only for illustrative purposes, and various schemes for determining similarity between the differential spectral image and each of the feature spectral images may be used based on some embodiments of the disclosed technology.

As described above, although the scheme for determining external gas using the captured spectral image and the feature spectral image is similar to the scheme for determining external gas using the captured image and the feature image shown in FIGS. 9 and 10, the scope of the disclosed technology is not limited thereto, and the scheme for determining external gas using the captured spectral image and the feature spectral image may be carried out without capturing the standard color chart 400. The above-mentioned scheme may be used to determine external gas based on the amount of change in the currently-captured spectral image by referring to the prestored reference spectral image. As a result, the change in refractive index of the air grid caused by inflow of external gas for each wavelength can be detected without using the standard color chart 400 providing a separate reference image, such that the resultant external gas can be recognized and determined.

Figure 12:
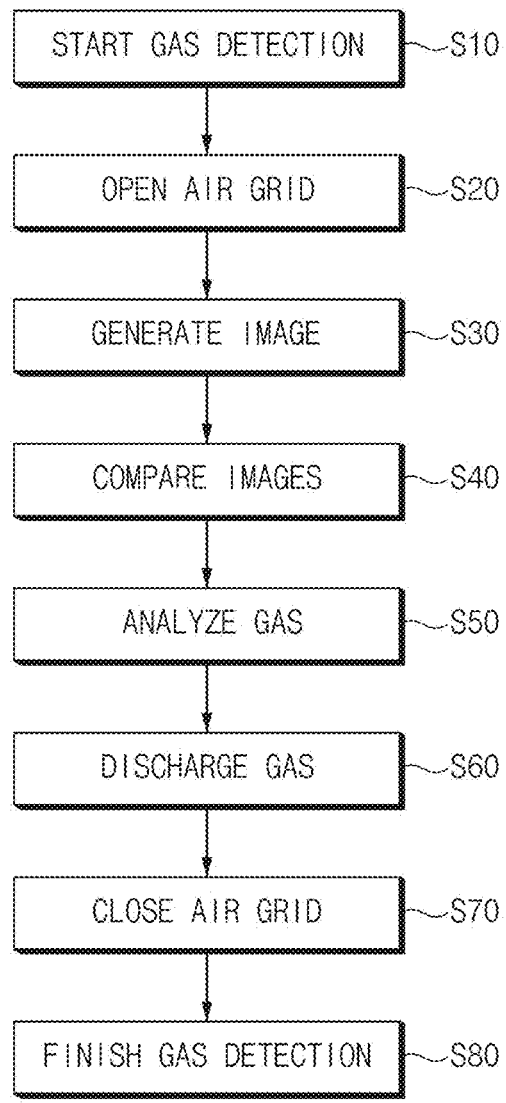
FIG. 12 is a flowchart illustrating a gas detection operation based on some embodiments of the disclosed technology.

FIG. 12 is a flowchart illustrating the gas detection operation based on an embodiment of the disclosed technology.

Referring to FIG. 12, the gas detection controller 200 may start the gas detection operation based on a user request or a predetermined internal interrupt signal (S10).

The gas detection controller 200 may control the grid shutter 300 to open the gas inlet passage in a manner that external gas can be introduced into the air grid of the image sensor 100 (S20).

The image sensor 100 may acquire an image corresponding to the target object under control of the gas detection controller 200 (S30). In this case, the light emitter 50 may emit light toward the target object under control of the gas detection controller 200.

The gas detection controller 200 may receive the captured image acquired by the image sensor 100, and may compare the captured image with a plurality of feature images (S40). In some embodiments, the gas detection controller 200 may receive the captured spectral image acquired by the image sensor 100, such that the gas detection controller 200 may compare a differential spectral image between the captured spectral image and the reference spectral image with the plurality of feature images.

The gas detection controller 200 may determine any one of the plurality of feature images based on the result of comparison between the captured image and each of the plural feature images, and may determine external gas corresponding to the determined feature image to be external gas flowing into the air region of the current image sensor 100 (S50). In some embodiments, the gas detection controller 200 may determine any one of the plurality of feature spectral images based on the result of comparison between the differential spectral image and each of the plural feature spectral images, and may identify the gas corresponding to the determined feature spectral image as the gas flowing into the air region of the current image sensor 100.

After completion of such determination of external gas, the gas detection controller 200 may control the grid shutter 300, so that external gas introduced into the air grid is discharged through the opened gas inlet passage either until a predetermined time (e.g., minute) has elapsed or until a specific condition (e.g., a condition in which characteristics of the newly acquired image are similar to those of the case in which external gas flowing into the air region is not present) has been satisfied (S60).

If a predetermined time has elapsed or if a specific condition has been satisfied, the gas detection controller 200 may control the grid shutter 300 to close the gas inlet passage (S70), such that the gas detection operation can be finished (S80).

The electronic device 10 including an image sensor with an air grid structure based on the embodiments of the disclosed technology can identify external gas using the air grid structure contained in the image sensor without using a separate sensor dedicated for gas detection.

What is claimed is:

1. An electronic device comprising:
an image sensor including at least one grid structure that extends in rows and columns of a pixel array including a plurality of imaging pixels and is structured to separate the imaging pixels from one another to provide optical isolation between two adjacent imaging pixels;
a grid shutter coupled to the grid structure and configured to allow a gas to enter the grid structure by opening a passage for the gas or block the gas from entering the grid structure by closing the passage in the grid structure; and
a gas detection controller configured to identify the gas flowing into the grid structure based on an image that is acquired by the image sensor when the passage for the gas in the grid structure is opened to allow the gas to be present in the grid structure.

2. The electronic device according to claim 1, wherein the grid structure includes a void space configured to optically isolate the imaging pixels from one another and configured to receive the gas through the grid shutter.

3. The electronic device according to claim 1, wherein the image acquired by the image sensor is a captured image photographed by a standard color chart.

4. The electronic device according to claim 3, wherein the gas detection controller compares the captured image with a plurality of prestored feature images, and identify the gas based on the result of comparison.

5. The electronic device according to claim 4, wherein each of the plurality of feature images is formed by experimentally acquiring the captured image about the standard color chart in a situation in which gas corresponding to each feature image is introduced into the grid structure.

6. The electronic device according to claim 1, wherein the image acquired by the image sensor is a captured spectral image indicating spectral characteristics.

7. The electronic device according to claim 6, wherein the gas detection controller compares an image corresponding to the result of calculation between the captured spectral image and a reference spectral image with a plurality of prestored feature spectral images, and identifies the gas according to the result of comparison.

8. The electronic device according to claim 7, wherein the reference spectral image is a spectral image in a situation in which the gas is not introduced into the grid structure.

9. The electronic device according to claim 7, wherein each of the plurality of feature spectral images is formed by experimentally acquiring information regarding changes in spectral images affected by inflow of the gas in a situation in which gas corresponding to each feature spectral image is introduced into the grid structure.

10. The electronic device according to claim 1, further comprising:
a light emitter configured to emit light toward a target object under control of the gas detection controller.

11. The electronic device according to claim 1, wherein the grid structure includes:
an air region filled with gas;
a capping film configured to surround the air region; and
a supporting film configured to surround the capping film.

12. The electronic device according to claim 11, wherein the grid structure is disposed between color filters contiguous to each other.

13. The electronic device according to claim 12, wherein:
a refractive index of each of the capping film and the supporting film is less than a refractive index of the color filter.

14. The electronic device according to claim 12, wherein the grid structure is formed to protrude outward at a position located between microlenses corresponding to the contiguous color filters.

15. The electronic device according to claim 11, wherein the grid structure is disposed below color filters contiguous to each other.

16. The electronic device according to claim 11, further comprising:

an over-coating layer disposed between grid structures contiguous to each other.

17. The electronic device according to claim 1, wherein the grid structure is disposed between spectral filters arranged either in a row direction or in a column direction of the pixel array, and each of the spectral filters is configured to allow a predetermined wavelength band to pass therethrough.

18. The electronic device according to claim 1, wherein:
the grid structure includes an opening portion needed for connection to the grid shutter,
wherein the opening portion is disposed at a side surface of a unit pixel including the grid structure.

19. The electronic device according to claim 1, wherein:
the grid structure includes an opening portion needed for connection to the grid shutter,
wherein the opening portion is disposed at a top surface of a unit pixel including the grid structure.

20. An electronic device comprising:
an image sensor including at least one grid structure disposed between color filters contiguous to each other and including a void space structured to receive and temporarily hold external gas; and
a gas detection controller configured to identify the external gas flowing into the void space of the grid structure based on an image that is acquired by the image sensor in a situation in which the grid structure is holding the external gas in the void space.

* * * * *